United States Patent
Okamoto et al.

(10) Patent No.: US 9,656,935 B2
(45) Date of Patent: May 23, 2017

(54) POLYOL-ETHER COMPOUND AND METHOD FOR PRODUCING THE SAME

(71) Applicant: MITSUBISHI GAS CHEMICAL COMPANY, INC., Chiyoda-ku (JP)

(72) Inventors: Atsushi Okamoto, Niigata (JP); Hideyuki Sato, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 14/785,227

(22) PCT Filed: Apr. 17, 2014

(86) PCT No.: PCT/JP2014/060930
§ 371 (c)(1),
(2) Date: Oct. 16, 2015

(87) PCT Pub. No.: WO2014/171511
PCT Pub. Date: Oct. 23, 2014

(65) Prior Publication Data
US 2016/0083321 A1    Mar. 24, 2016

(30) Foreign Application Priority Data
Apr. 18, 2013 (JP) .................................. 2013-087738

(51) Int. Cl.
*C07C 41/28* (2006.01)
*C07C 43/13* (2006.01)

(52) U.S. Cl.
CPC ............ *C07C 41/28* (2013.01); *C07C 43/132* (2013.01)

(58) Field of Classification Search
CPC ............................. C07C 41/28; C07C 43/132
See application file for complete search history.

(56) References Cited

U.S. PATENT DOCUMENTS

| | | |
|---|---|---|
| 3,092,640 A | 6/1963 | Mantell et al. |
| 3,287,419 A | 11/1966 | Duke, Jr. et al. |
| 5,780,687 A | 7/1998 | Holderich et al. |
| 5,821,391 A | 10/1998 | Holderich et al. |

FOREIGN PATENT DOCUMENTS

| | | |
|---|---|---|
| EP | 1 598 357 A1 | 11/2005 |
| EP | 1 772 451 A1 | 4/2007 |
| JP | 10-67698 A | 3/1998 |
| JP | 2009-173551 A | 8/2009 |
| WO | 01/14300 A1 | 3/2001 |

OTHER PUBLICATIONS

International Search Report Issued Jul. 22, 2014 in PCT/JP14/060930 Filed Apr. 17, 2014.

*Primary Examiner* — Rosalynd Keys
(74) *Attorney, Agent, or Firm* — Oblon, McClelland, Maier & Neustadt, L.L.P.

(57) ABSTRACT

A method for producing a polyol-ether compound, wherein a compound represented by the following formula (1) is subjected to hydrogenation reduction in the presence of a hydrogenation catalyst to obtain a polyol-ether compound having a skeleton represented by the following formula (2):

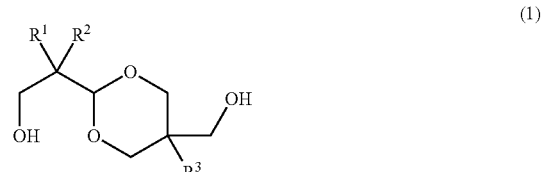

(1)

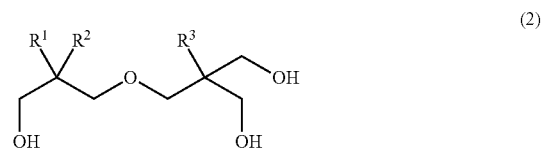

(2)

wherein $R^1$ and $R^2$, which may be the same as or different from each other, each represent a linear or branched alkyl group having 1 to 6 carbon atoms; and $R^3$ represents a linear or branched alkyl group having 1 to 6 carbon atoms or a hydroxymethyl group.

20 Claims, No Drawings

POLYOL-ETHER COMPOUND AND METHOD FOR PRODUCING THE SAME

TECHNICAL FIELD

The present invention relates to a polyol-ether compound and a method for producing the same.

BACKGROUND ART

Up to present, various compounds have been synthesized and widely used in the industrial field as a polyol-ether compound having a plurality of hydroxyl groups and an ether bond in combination in a molecule. Among these, di-trimethylolpropane, di-pentaerythritol and the like are known as a compound having at least three primary hydroxyl groups and an ether bond in combination. The demand for these compounds has recently increased and thus they are important compounds.

Not many methods for producing a polyol-ether compound having at least three hydroxyl groups and an ether bond in combination are disclosed in prior art documents. One of the methods is disclosed in Examples of Patent Document 1. In Example 7 of Patent Document 1, a method for obtaining neopentylglycol-trimethylolpropane ether from a condensation reaction between trimethylolpropane oxetane and neopentylglycol through open-ring reaction of trimethylolpropane oxetane is disclosed as the method for producing a polyol-ether compound. Patent Document 2 discloses (1) that an aliphatic polyalcohol is susceptible to hydrogenolysis in the presence of a specific hydrogenation catalyst and (2) that a terminal primary hydroxyl group is susceptible to hydrogenolysis.

CITATION LIST

Patent Document

Patent Document 1: International Publication No. WO 2001/14300
Patent Document 2: Japanese Patent Application Laid-Open No. 2009-173551

SUMMARY OF INVENTION

Technical Problem

At present, di-trimethylolpropane is obtained as a by-product from a manufacturing plant for trimethylolpropane and di-pentaerythritol from a manufacturing plant for pentaerythritol. Accordingly, these cannot be singly produced. In the circumstance, it has been desired to develop a method for producing a polyol-ether compound independent of production amount of other compounds.

By-products polyol-ether compounds such as di-trimethylolpropane and di-pentaerythritol have a symmetrical structure such as a dimerized structure of trimethylolpropane and a dimerized structure of pentaerythritol, respectively. Because of this, it has been desired to develop a method of producing a polyol-ether compound, in which the number and arrangement of hydroxyl groups and the polarity and symmetry of a molecule can be changed depending on different usages.

In the method for producing a polyol-ether compound disclosed in Patent Document 1, an oxetane compound as a raw material is expensive. In addition, the oxetane compound has high reactivity and a secondary reaction easily takes place. As a result, a reaction selectivity of a polyol-ether compound decreases. This is a problem with this method.

Neopentyl glycol-trimethylolpropane ether as disclosed in Patent Document 1 is one of polyol-ether compounds having three primary hydroxyl groups and an ether bond in combination and a structure where the hydroxyl groups are arranged asymmetrically to the ether bond. Since the three hydroxyl groups of the compound are distributed in a ratio of 1:2 to the ether bond, the compound can be used for synthesizing a specifically branched and useful polymer compound represented by, for example, a dendrimer. However, to synthesize a further highly and specifically branched polymer compound, it is desired to develop a polyol-ether compound having a further larger number of hydroxyl groups asymmetrically arranged to an ether bond in a higher distribution ratio.

An object of the present invention is to provide a method for efficiently producing a polyol-ether compound by overcoming the aforementioned problems in the art and to provide a novel polyol-ether compound obtained by the production method.

Solution to Problem

The present inventors have conducted intensive studies on a method for efficiently producing a polyol-ether compound. As a result, they found a method for efficiently producing a polyol-ether compound by hydrogenating a specific cyclic acetal compound in the presence of a hydrogenation catalyst and arrived at the present invention.

More specifically, the present invention is as follows.

<1> A method for producing a polyol-ether compound, wherein a compound represented by the following formula (1) is subjected to hydrogenation reduction in the presence of a hydrogenation catalyst to obtain a polyol-ether compound represented by the following formula (2):

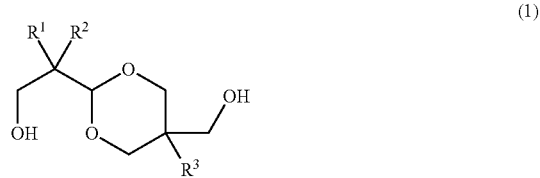

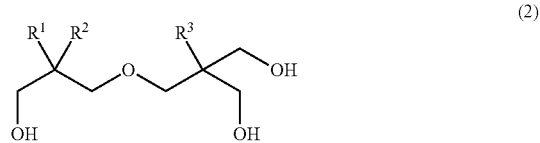

wherein $R^1$ and $R^2$, which may be the same as or different from each other, each represent a linear or branched alkyl group having 1 to 6 carbon atoms; and $R^3$ represents a linear or branched alkyl group having 1 to 6 carbon atoms or a hydroxymethyl group.

<2> The method according to <1>, in which the $R^3$ is a methyl group or an ethyl group.
<3> The method according to <1>, in which the $R^3$ is a hydroxymethyl group.
<4> The method according to any one of <1> to <3>, in which the $R^1$ and the $R^2$ are each a methyl group.
<5> The method according to any one of <1> to <4>, in which the compound represented by the general formula (1) is subjected to hydrogenation reduction in a reaction solvent containing at least one selected from the group consisting of ether compounds and saturated hydrocarbon compounds.

<6> The method according to any one of <1> to <5>, in which the hydrogenation catalyst is a solid catalyst containing palladium.

<7> The method according to any one of <1> to <6>, in which the hydrogenation catalyst is a solid catalyst containing a zirconium compound or an apatite compound.

<8> A polyol-ether compound represented by the following formula (3):

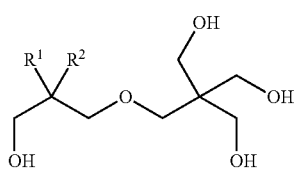

(3)

wherein $R^1$ and $R^2$, which may be the same as or different from each other, each represent a linear or branched alkyl group having 1 to 6 carbon atoms.

<9> The polyol-ether compound according to <8>, in which $R^1$ and $R^2$ are each a methyl group.

Advantageous Effects of Invention

The production method of the present invention makes it possible to efficiently produce a polyol-ether compound and to obtain a novel polyol-ether compound having an asymmetric structure.

DESCRIPTION OF EMBODIMENTS

Now, an embodiment of the present invention (hereinafter, simply referred to as "the present embodiment") will be described. Note that the following embodiment is an example illustrating the present invention and the present invention is not limited to the present embodiment alone. In the production method for a polyol-ether compound according to the present embodiment, a polyol-ether compound represented by the following formula (2) is obtained by hydrogenation reduction of a compound represented by the following formula (1) in the presence of a hydrogenation catalyst.

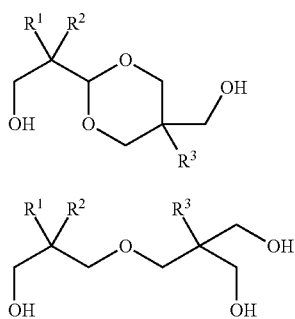

In the formula (1) and formula (2), $R^1$ and $R^2$, which may be the same as or different from each other, each represent a linear or branched alkyl group having 1 to 6 carbon atoms; and $R^3$ represents a linear or branched alkyl group having 1 to 6 carbon atoms or a hydroxymethyl group. The compound represented by formula (1) may sometimes have a plurality of geometric isomers. When $R^1$ and $R^2$ are different from each other, the compounds represented by the formula (1) and formula (2) have a plurality of optical isomers.

<Raw-material Compound>

A compound used as a raw-material in a method for producing a polyol-ether compound of the present embodiment (hereinafter, also referred to simply as the "production method") is a six-membered cyclic acetal compound (hereinafter, referred to as a "compound (1)") having a 1,3-dioxane skeleton and represented by the general formula (1) above.

A raw-material for synthesizing a compound (1) or a process to be used in the present embodiment is not particularly limited and compounds produced by methods known in the art can be used. The simplest and most efficient method for producing a compound (1) is a method comprising cyclodehydration of 2-hydroxymethyl-2-substituted-1,3-propanediol or pentaerythritol (2,2-bis-hydroxymethyl-propane-1,3-diol) and 3-hydroxy-2,2-disubstituted-propionaldehyde in the presence of an acid catalyst and the like. Other than this, the method for producing a compound (1) may be a production method based on an acetal exchange reaction between 2-hydroxymethyl-2-substituted-1,3-propanediol or pentaerythritol and a lower alcohol acetal of 3-hydroxy-2,2-disubstituted-propionaldehyde.

Examples of 3-hydroxy-2,2-disubstituted-propionaldehyde which can be employed for producing the compound (1) by cyclodehydration of 3-hydroxy-2,2-disubstituted-propionaldehyde and 2-hydroxymethyl-2-substituted-1,3-propanediol, include:
3-hydroxy-2,2-dimethyl-propionaldehyde;
3-hydroxy-2,2-diethyl-propionaldehyde;
3-hydroxy-2-methyl-2-ethyl-propionaldehyde;
3-hydroxy-2-methyl-2-propyl-propionaldehyde;
3-hydroxy-2-methyl-2-butyl-propionaldehyde;
3-hydroxy-2-ethyl-2-butyl-propionaldehyde;
3-hydroxy-2-propyl-2-pentyl-propionaldehyde; and
3-hydroxy-2-methyl-2-hexyl-propionaldehyde.

Substituents bonded to a carbon atom at the 2-position of a propionaldehyde skeleton correspond to $R^1$ and $R^2$ in the general formula (1).

Examples of the 2-hydroxymethyl-2-substituted-1,3-propanediol that can be applied in this case include:
2-hydroxymethyl-2-methyl-1,3-propanediol (trimethylolethane);
2-hydroxymethyl-2-ethyl-1,3-propanediol (trimethylol propane);
2-hydroxymethyl-2-propyl-1,3-propanediol;
2-hydroxymethyl-2-butyl-1,3-propanediol;
2-hydroxymethyl-2-pentyl-1,3-propanediol;
2-hydroxymethyl-2-hexyl-1,3-propanediol; and
pentaerythritol (2,2-bis-hydroxymethyl-propane-1,3-diol).

To the carbon atom at the 2-position of 1,3-propanediol, a hydroxymethyl group and the substituent corresponding to $R^3$ in the above formula (1) are bonded.

Examples of each of $R^1$ and $R^2$ in the above general formula (1) include a methyl group, an ethyl group, a n-propyl group, a 1-methylethyl group (isopropyl group), a n-butyl group, a 1-methylpropyl group, a 2-methylpropyl group, a 1,1-dimethylethyl group (tert-butyl group), a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group (neopentyl group), a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group and a 1-ethyl-2-methylpropyl group. Of these, $R^1$ and $R^2$ are preferably each independently a methyl group, an ethyl group, a n-propyl group or a 1-methylethyl group (isopropyl group) and $R^1$ and $R^2$ are more preferably both methyl groups.

Examples of $R^3$ in the above general formula (1) include a methyl group, an ethyl group, a n-propyl group, a 1-methylethyl group (isopropyl group), a n-butyl group, a 1-methylpropyl group, a 2-methylpropyl group, a 1,1-dimethylethyl group (tert-butyl group), a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group (neopentyl group), a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group and a hydroxymethyl group. Of these, $R^3$ is preferably a methyl group, an ethyl group, a n-propyl group, a 1-methylethyl group (isopropyl group), a n-butyl group, a 1-methylpropyl group, a 2-methylpropyl group, a 1,1-dimethylethyl group (tert-butyl group) or a hydroxymethyl group, and more preferably a methyl group, an ethyl group or a hydroxymethyl group.

As a combination of $R^1$, $R^2$ and $R^3$, the aforementioned examples may be used in any combination.

According to the present embodiment, when the substituent of a compound (1) is appropriately selected, e.g., the number of hydroxyl groups and the polarity of a molecule can be changed and only a desired polyol-ether compound suitable for industrial application can be advantageously produced.

According to the present embodiment, two or more polyol-ether compounds may be produced by using two or more compounds (1). In this case, the combination or ratio of two or more compounds (1) is not particularly limited.

<Hydrogenation Catalyst>
I. Specific Metal Component

Examples of active ingredients of the hydrogenation catalyst used in the present embodiment include a metal element having a catalytic hydrogenation property (hereinafter, referred to as a "specific metal component"). Examples of the specific metal component include nickel, cobalt, iron, ruthenium, rhodium, palladium, platinum, iridium, copper, silver, molybdenum, tungsten, chromium, and rhenium. As long as the specific metal component exhibits a hydrogenation property, the specific metal component may be in a metal state or in a cation state.

Among these, since the hydrogenation property of the specific metal component in the metal state is generally higher, and the specific metal component is more stable under a reduction atmosphere, the specific metal component is preferably in the metal state. The specific metal components may be used either singly or in combinations of two or more in a state where the specific metal components are contained in a solid catalyst. When the two or more specific metal components are used, the combination, mixing ratio, and form of the specific metal components are not particularly limited, and the specific metal components may be used in a form such as a mixture, alloy or intermetallic compound of metals.

In the present embodiment, the hydrogenation catalyst is preferably a solid catalyst containing at least one specific metal component selected from the group consisting of palladium, platinum, nickel and copper, and particularly preferably a solid catalyst containing palladium as the specific metal component.

Raw materials of the specific metal components are not particularly limited. Raw materials used when the catalyst is prepared by a conventionally known method can be employed. Examples of the raw materials include hydroxides, oxides, fluorides, chlorides, bromides, iodides, sulfates, nitrates, acetates, ammine complexes, and carbonyl complexes of metal elements. These are used either singly or in combinations of two or more.

In the hydrogenation catalyst of the present embodiment, the specific metal component as the metal component may also be used either singly or in combinations with another metal element having no catalytic hydrogenation property. Examples of the catalyst using a single specific metal component include a catalyst such as palladium black or platinum black including a metal fine powder of the specific metal component. Examples of the catalyst including a specific metal component and another metal element having no catalytic hydrogenation property in combination, a sponge catalyst, which is prepared by forming an alloy from the specific metal component, aluminum and a small amount of additive, and thereafter leaching all or part of aluminum.

II. Specific Addition Component

In order to further improve the activity, selectivity, and physical properties or the like of the catalyst, the specific metal component and the following components may also be added to the catalyst and used: lithium, sodium, potassium, rubidium, and cesium as an alkali metal element; magnesium, calcium, strontium, and barium as an alkaline-earth metal element; fluoride, chlorine, bromine, and iodine as a halogen element; and a compound of one or two or more elements selected from the group consisting of mercury, lead, bismuth, tin, tellurium, and antimony as an auxiliary added element (hereinafter, referred to as a specific addition component).

Raw materials of these specific addition components are not particularly limited. Raw materials used when the catalyst is prepared by a conventionally known method can be employed. Examples of the raw materials include hydroxides, oxides, fluorides, chlorides, bromides, iodides, sulfates, nitrates, acetates, and ammine complexes of metal elements. These are used either singly or in combinations of two or more. An addition method of the specific addition component, and a ratio of the specific addition component to the specific metal component are not also particularly limited.

III. Specific Non-metal Component

In the hydrogenation catalyst of the present embodiment, the specific metal component may also be used in combination with a non-metal substance. Main examples of the non-metal substance include an elementary substance, carbide, nitride, oxide, hydroxide, sulfate, carbonate, and phosphate (hereinafter, referred to as a "specific non-metal component"). Specific examples thereof include graphite, diamond, activated carbon, silicon carbide, silicon nitride, aluminum nitride, boron nitride, boron oxide, aluminum oxide (alumina), silicon oxide (silica), titanium oxide, zirconium oxide, hafnium oxide, lanthanum oxide, cerium oxide, yttrium oxide, niobium oxide, magnesium silicate, calcium silicate, magnesium aluminate, calcium aluminate, zinc oxide, chromic oxide, alumino silicate, aluminosilico phosphate, alumino phosphate, borophosphate, magnesium phosphate, calcium phosphate, strontium phosphate, apatite hydroxide (hydroxy calcium phosphate), apatite chloride, apatite fluoride, calcium sulfate, barium sulfate, and barium carbonate. The specific non-metal component is used either singly or in combinations of two or more. When the specific non-metal components are used in combinations of two or more, the combination, mixing ratio, and form of the specific non-metal components are not particularly limited, and the specific non-metal components may be used in a form such as a mixture, composite compound, or double salt of materials.

From the viewpoint of industrial use, a specific non-metal component obtained simply and inexpensively is preferable. The specific non-metal component is preferably a zirconium compound, an aluminum compound, and an apatite compound, and more preferably a zirconium compound and an apatite compound. Among these, the specific non-metal component is particularly preferably zirconium oxide and apatite hydroxide (hydroxy calcium phosphate). Furthermore, a part or all of these specific non-metal components to be used may be modified or ion-exchanged by using the above-mentioned specific addition component.

Carbide, nitride and oxide or the like of the specific metal component can be used as the specific non-metal component. However, when these are exposed to a hydrogenation reduction atmosphere, they are partly reduced to metals. In such a case, a part thereof serves as a specific metal component and the remaining part serves as a non-metal component. Also, such a substance can be used. Examples in the case include oxides such as nickel oxide, iron oxide, cobalt oxide, molybdenum oxide, tungstic oxide, and chromic oxide.

IV. Hydrogenation Catalyst

The specific metal component may be singly used as the hydrogenation catalyst of the present embodiment; the specific metal component and the specific non-metal component may be used in combination; and the hydrogenation catalyst may contain the specific addition component, besides these, in some cases. The producing method of the hydrogenation catalyst of the present embodiment is not particularly limited, and a conventionally known method can be used. Examples thereof include a method for impregnating the specific non-metal component with the raw material compound of the specific metal component (supporting method), a method for dissolving both the raw material compound of the specific metal component and the raw material compound of the specific non-metal component in a suitable solvent, and simultaneously depositing the specific metal component and the specific non-metal component by using an alkali compound or the like (coprecipitation method), and a method for mixing and uniformizing the raw material compound of the specific metal component and the specific non-metal component at a suitable ratio (kneading method).

Depending on the composition of the hydrogenation catalyst or the convenience of the catalyst preparation method, the specific metal component can be prepared in a cation state, and then reduced to bring the specific metal component into a metal state. A conventionally known reduction method and reducing agent can be used therefor, and are not particularly limited. Examples of the reducing agent include reducing inorganic gas such as hydrogen gas, carbon monoxide gas, ammonia, hydrazine, phosphine, or silane, a lower oxygen-containing compound such as methanol, formaldehyde, or formic acid, and hydride such as sodium boron hydride or aluminum lithium hydride. The specific metal component is changed to the metal state by reducing the specific metal component in the cation state in a gas phase or a liquid phase in which these reducing agents are present. The reduction processing condition at this time can be set to a suitable condition depending on the kinds and quantities or the like of the specific metal component and reducing agent. The reduction processing may be separately operated by using a catalyst reduction equipment before the hydrogenation reduction in the producing method of the present embodiment, or may be operated before reaction start or simultaneously with reaction operation, in a reactor vessel used for the producing method of the present embodiment.

The metal content and shape of the hydrogenation catalyst of the present embodiment are not also particularly limited. In terms of the shape, the hydrogenation catalyst may be a powder or may be molded. The shape of the molded hydrogenation catalyst and the molding method are not particularly limited. For example, a spherical product, a tablet molded product, and an extrusion molded product, and a product obtained by crushing those products to a suitable size may be appropriately selected and used.

The specific metal component is particularly preferably palladium. Hereinafter, a catalyst including palladium will be described in detail.

When the specific metal component is palladium, considering that palladium is a noble metal, it is economically desired that the amount of palladium to be used is small, and palladium is effectively utilized. Therefore, it is preferable that palladium is used in a state where it is dispersibly supported on a catalyst carrier.

A palladium compound as a raw material of palladium is suitably a palladium compound which is soluble in water or an organic solvent. Examples of the palladium compound include palladium chloride, a tetrachloropalladium salt, a tetraamminepalladium salt, palladium nitrate, and palladium acetate. Among these, palladium chloride is preferable as it has high solubility in water or an organic solvent and is likely to be industrially utilized. Palladium chloride can be used after dissolved in an aqueous solution of sodium chloride, diluted hydrochloric acid, and ammonia water or the like.

The solution of the palladium compound is added to the catalyst carrier, or the catalyst carrier is immersed in the solution of the palladium compound, to fix palladium or the palladium compound on the catalyst carrier. General examples of the fixing method include adsorption to a carrier, crystallization by removing a solvent by distillation, and precipitation-deposition using a reducing substance and/or a basic substance acting on the palladium compound. A suitable method is appropriately used for the fixing method. The content of palladium in the hydrogenation catalyst prepared by the method is preferably 0.01 to 20% by mass, more preferably 0.1 to 10% by mass, and still more preferably 0.5 to 5% by mass in terms of metal palladium based on the total amount of the hydrogenation catalyst. When the content of palladium is 0.01% by mass or more, a more sufficient hydrogenation rate is obtained, and the conversion of the compound (1) tends to be further increased. On the other hand, when the content of palladium is 20% by mass or less, dispersion efficiency of palladium in the hydrogenation catalyst tends to be further increased, and palladium can be more effectively used.

Depending on the convenience of the palladium compound or the catalyst preparation method, palladium may be supported on the carrier not in a metal state but in a cation state. In that case, supported palladium as a cation (for example, present in a state of the palladium compound) can also be used after being reduced to metal palladium. A conventionally known reduction method and reducing agent can be employed therefor, and are not particularly limited. Examples of the reducing agent include reducing inorganic gases such as hydrogen gas, carbon monoxide gas, ammonia, and hydrazine, lower oxygen-containing compounds such as methanol, formaldehyde, and formic acid, hydrocarbon compounds such as ethylene, propylene, benzene, and toluene, and hydrides such as sodium boron hydride and aluminum lithium hydride. Palladium as the cation can be easily reduced to metal palladium by bringing palladium into contact with the reducing agent in a gas phase or a liquid phase. The reduction processing condition at this time can be set to a suitable condition by the kind and quantity or the like of the reducing agent. The reduction processing may be separately operated by using a catalyst reduction equipment before the hydrogenation reduction in the producing method of the present embodiment, or may be operated before reaction start or simultaneously with reaction operation in a reactor vessel used for the producing method of the present embodiment.

One kind of the specific non-metal component used with the specific metal component of the present embodiment is preferably a zirconium compound. The hydrogenation catalyst containing the zirconium compound will be described in detail below.

The zirconium compound used for the present embodiment is preferably obtained by using one selected from the group consisting of zirconium oxide, zirconium hydroxide, zirconium carbonate, alkaline earth zirconate salts, rare earth zirconate salts, and zircon, alone or a combination of two or more thereof.

The zirconium compound is particularly preferably zirconium oxide, and a method for producing zirconium oxide is not particularly limited. For example, a method for decomposing an aqueous solution of a soluble zirconium salt by a basic substance to produce zirconium hydroxide or zirconium carbonate, and thereafter thermally decomposing zirconium hydroxide or zirconium carbonate to prepare zirconium oxide is known as a general method. Examples of raw materials of the zirconium compound at this time include, but are not limited to, zirconium oxychloride, zirconium oxynitrate, zirconium chloride, zirconium sulfate, zirconium tetraalkoxide, zirconium acetate, and zirconium acetylacetonato. These are used either singly or in combinations of two or more. Examples of the basic substance used for decomposition include ammonia, alkylamines, ammonium carbonate, ammonium hydrogen carbonate, sodium hydroxide, sodium carbonate, sodium hydrogen carbonate, potassium hydrate, potassium carbonate, potassium hydrogen carbonate, manganese hydroxide, calcium hydroxide, lanthanum hydroxide, yttrium hydroxide, and cerium hydroxide. These are used either singly or in combinations of two or more.

When zirconium oxide is used as the specific non-metal component, the physical properties and shape thereof are not particularly limited. The purity of zirconium oxide is not also particularly limited, and a commercially available general-purpose product and a high purity product can be appropriately used.

Another kind of the specific non-metal component used with the specific metal component of the present embodiment is preferably an apatite compound. The hydrogenation catalyst containing the apatite compound will be described in detail below.

Examples of the apatite compound used for the present embodiment include a hexagonal compound having a composition of $M_{10}(ZO_4)_6X_2$ described in the academic journal "Syokubai (Catalysts & Catalysis)," 27 (4), 237-243 (1985). Herein, examples of M include calcium, strontium, aluminum, yttrium, lanthanum, and cerium. Examples of Z include phosphorus, arsenic, vanadium, and chromium. Examples of X include a hydroxyl group, a carbonate group, fluoride, chlorine, bromine, and iodine. All of M, Z, and X may contain one or two or more of the above within a range of restriction on a physical structure by an ion radius or the like. The apatite compound is also known to have a non-stoichiometric composition. The apatite compound of the present embodiment includes also the non-stoichiometric composition. The non-stoichiometric composition is represented by the general formula of $M_{10-a}(HZO_4)_a(ZO_4)_{6-a}X_{2-a}$ where $0<a\leq 1$ is set.

Among these, it is preferable that M is calcium and Z is phosphorus. The producing method of the apatite compound having calcium and phosphorus is not particularly limited, and a conventionally known method can be used. Examples of the method include a method for sufficiently mixing a suitable phosphate and calcium salt at a stoichiometric ratio, and thereafter heating them (solid phase method), a method for mixing a calcium cation-containing solution and a phosphate anion-containing solution under a basic condition to obtain a precipitation (precipitation method), a method for hydrolyzing calcium phosphate having poor water solubility as a starting material under a basic condition to convert calcium phosphate into apatite (hydrolysis method), and a method for hydrothermally processing calcium phosphate having poor water solubility in a sealing pressure tight case (hydrothermal synthesis method). A suitable method is appropriately employed.

The apatite compound has anion exchangeability. It is known that a portion equivalent to X can be easily anion-exchanged even after being synthesized as the apatite compound. The apatite compound of the present embodiment includes calcium phosphate apatite having one or two or more anions such as a carbonate group, a bicarbonate group, a hydroxyl group, chloride, and fluoride, and having a part or all thereof exchanged with anions different from that during synthesizing. At least a part of anions of the apatite compound may be exchanged by, for example, a method for synthesizing hydroxylated calcium phosphate, and bringing a solution containing chloride or fluoride ions into contact therewith, or a method for bringing anions contained as a part of raw materials of a specific metal component or a specific addition component into contact with the apatite compound when supporting a specific metal component or a specific addition component on the apatite compound used as a carrier. A starting material in ion exchange treatment at this time, a concentration, and a processing condition or the like are not particularly limited. A suitable method is appropriately used.

When the specific non-metal component typified by the zirconium compound and the apatite compound is used as the catalyst carrier, the shapes and values of physical properties such as particle diameters and porosities of these carriers, and a method for supporting a metal component, or the like are not particularly limited. A shape suitable for a reaction method and a condition, physical properties of the carrier, and a support method or the like can be appropriately selected and used.

When these compounds are used as a catalyst carrier, the BET specific surface area of the carrier is not particularly limited. The carrier having a general specific surface area of approximately 0.1 to 400 m²/g can be used. The carrier having a specific surface area of 1 to 300 m²/g is preferable and the carrier having a specific surface area of 10 to 200 m²/g is more preferable.

For the solvent used for the hydrogenation reduction of the present embodiment, a reaction may be performed under a non-solvent environment using only the compound (1) which is the raw material, or a reaction solvent may be used. When the reaction solvent to be used is in a state inactive for hydrogenation reduction, the kind and concentration thereof are not particularly limited. However, when a reaction solvent having higher interaction with the specific metal component in the hydrogenation catalyst than that of the compound (1) is used, the reaction rate may be extremely decreased or the reaction may stop. From the viewpoint, it is preferable that a compound containing, for example, phosphorus, nitrogen, and sulfur is not used as the reaction solvent. However, the reaction solvent may be used in an amount small enough that it does not greatly influence the reaction rate. The reaction solvent is preferably a saturated hydrocarbon compound, an ester compound and an ether compound. A saturated hydrocarbon compound and an ether compound are more preferable. These are used either singly or in combinations of two or more.

Examples of the reaction solvent include n-pentane, iso-pentane, n-hexane, iso-hexane, 2,2-dimethyl-butane, n-heptane, iso-heptane, 2,2,4-trimethylpentane, n-octane, iso-octane, n-nonane, iso-nonane, its isomer, n-decane, n-pentadecane, cyclohexane, methylcyclohexane, dimethyl-cyclohexane, its isomer, and decalin as the saturated hydrocarbon compound; methyl acetate, ethyl acetate, butyl acetate, methyl propionate, n-methyl butyrate, n-ethyl butyrate, n-butyl butyrate, i-methyl butyrate, n-cyclohexyl butyrate, i-cyclohexyl butyrate, methyl valerate, and its isomer as the ester compound; and dimethyl ether, diethyl ether, di-n-propyl ether, di-iso-propyl ether, di-n-butyl ether, di-iso-butyl ether, di-sec-butyl ether, methyl propyl ether, ethyl propyl ether, methyl butyl ether, methyl pentyl ether, ethyl butyl ether, propyl butyl ether, methyl cyclopentyl ether, methyl cyclohexyl ether, ethyl cyclopentyl ether, ethyl cyclohexyl ether, propyl cyclopentyl ether, propyl cyclohexyl ether, butyl cyclopentyl ether, butyl cyclohexyl ether, ethylene glycol dimethyl ether, ethylene glycol diethyl ether, propylene glycol dimethyl ether, propylene glycol diethyl ether, diethylene glycol dimethyl ether, diethylene glycol diethyl ether, triethylene glycol dimethyl ether, triethylene glycol diethyl ether, tetrahydrofuran, methyl tetrahydrofuran, tetrahydropyran, methyl tetrahydropyran, 1,4-dioxane, dimethyl-1,4-dioxane, and their isomers as the ether compound. Note that the saturated hydrocarbon compound serving as the reaction solvent include a linear, branched and cyclic alkanes.

Among these, one or more selected from the group consisting of n-pentane, iso-pentane, n-hexane, iso-hexane, 2,2-dimethyl-butane, n-heptane, iso-heptane, dimethyl ether, diethyl ether, di-n-propyl ether, di-iso-propyl ether, di-n-butyl ether, di-iso-butyl ether, di-sec-butyl ether, methyl propyl ether, tetrahydrofuran, methyltetrahydrofuran, tetrahydropyrane, methyltetrahydropyrane and 1,4-dioxane is preferable. At least one selected from the group consisting of di-iso-propyl ether, 1,4-dioxane and n-hexane is more preferable.

The reaction system of the hydrogenation reduction in the present embodiment is formed from the compound (1), or a liquid phase containing the compound (1) and the reaction solvent, a gas phase of hydrogen gas, and a solid phase of the hydrogenation catalyst. As long as the reaction scheme is performed in a state where these coexist, the reaction system is not particularly limited. Any one of conventionally known forms such as a tube type, a tank type, and a boiler type can be used as the type of a reaction vessel in the hydrogenation reduction of the present embodiment. A method for feeding a raw material composition may be any of a continuously feeding method and a batch method. Any one of conventionally known methods such as a fixed bed, a fluid bed, and a suspension bed can be employed for the hydrogenation catalyst, and the hydrogenation catalyst is not particularly limited. In the case of the fixed bed flow method, the reaction can be performed under a trickle flow condition and a bubble flow condition. The raw material liquid may be fed in the gravity direction (downflow) or in the opposite direction (upflow). The raw material gas and the raw material liquid may be fed in either a parallel manner or a countercurrent manner.

A reaction temperature in the hydrogenation reduction of the present embodiment is preferably 50 to 350° C., more preferably 100 to 300° C., and still more preferably 150 to 280° C. When the reaction temperature is 50° C. or more, a higher hydrogenation rate tends to be likely to be obtained. When the reaction temperature is 350° C. or less, the side reaction involving the decomposition of the raw material can be further suppressed, and the yield of the subject matter tends to be further increased.

A reaction pressure in the hydrogenation reduction of the present embodiment is preferably 0.1 to 30 MPa, and more preferably 2 to 15 MPa. When the reaction pressure is 0.1 MPa or more, a higher hydrogenation rate is likely to be obtained, and the conversion of the compound (1) tends to be improved. When the reaction pressure is 30 MPa or less, reaction facility cost can be suppressed lower, which tends to be economically preferable.

The hydrogen gas used for the hydrogenation reduction of the present embodiment may not be particularly highly refined, and may have quality usually used for an industrial hydrogenation reaction. A higher purity of hydrogen gas to be used is preferable since the hydrogenation reaction is promoted depending on hydrogen partial pressure. However, the hydrogen gas may be mixed with gas inert to the reaction such as helium, argon, nitrogen, and methane. A ratio of the hydrogen gas to the compound (1) in the reaction system is preferably 0.1 to 300, and more preferably 0.5 to 100 when the ratio is represented as a feed molar ratio of the hydrogen gas to the compound (1) in the case of a batch reaction and as a mole supply speed ratio of the hydrogen gas to the compound (1) in the case of a feeding reaction. When the feed molar ratio or the mole supply speed ratio of the hydrogen gas is 0.1 or more, the hydrogenation reaction tends to be further promoted. When the feed molar ratio or the mole supply speed ratio of the hydrogen gas is 300 or less, facility cost for cyclic use of excess hydrogen gas tends to be able to be suppressed lower.

Now, the polyol-ether compound of the present embodiment will be more specifically described.

As a polyol-ether compound having three primary hydroxyl groups and an ether bond in combination in a molecule (the primary hydroxyl groups are arranged asymmetrically to the ether bond), neopentyl glycol-trimethylolpropane ether disclosed in Patent Document 1 is known. The three hydroxyl groups of the compound is distributed in a ratio of 1:2 to the ether bond.

In contrast, a polyol-ether compound having three or more primary hydroxyl groups, which are arranged asymmetrically to an ether bond in a higher distribution ratio, is expected to be industrially used, for example, for synthesizing a specifically branched and useful polymer compound, such as a dendrimer, but is not known in the art.

According to the present embodiment, a polyol-ether compound having 4 primary hydroxyl groups, which are arranged asymmetrically to an ether bond in a distribution ratio of 1:3, can be easily and efficiently produced by the aforementioned production method, more specifically, by hydrogenation reduction of a compound represented by the following formula (A). The novel polyol-ether compound having an asymmetric structure, which can be produced by the present embodiment, include those represented by the following formula (B).

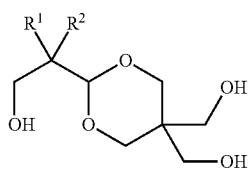

(A)

where $R^1$ and $R^2$, which may be the same as or different from each other, each represent a linear or branched alkyl group having 1 to 6 carbon atoms.

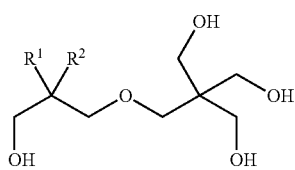

(B)

where $R^1$ and $R^2$ are the same as defined in the formula (A).

Examples of a compound represented by the formula (B) (hereinafter, referred to as compound (B)) include compounds represented by the above formula (B) where $R^1$ and $R^2$ each independently represent a methyl group, an ethyl group, a n-propyl group, a 1-methylethyl group (isopropyl group), n-butyl group, a 1-methylpropyl group, a 2-methylpropyl group, a 1,1-dimethylethyl group (tert-butyl group), a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group (neopentyl group), a n-hexyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group or a 1-ethyl-2-methylpropyl group.

Of these, a compound where $R^1$ and $R^2$ are each independently a methyl group, an ethyl group, a n-propyl group, a 1-methylethyl group (isopropyl group), a n-butyl group, a 1-methylpropyl group, a 2-methylpropyl group, a 1,1-dimethylethyl group (tert-butyl group), n-pentyl group, a 1-methylbutyl group, a 2-methylbutyl group, a 3-methylbutyl group, a 1-ethyl propyl group, a 1,1-dimethylpropyl group, a 1,2-dimethylpropyl group or a 2,2-dimethylpropyl group (neo pentyl group) is preferable and a compound where $R^1$ and $R^2$ both are a methyl group is more preferable.

A polyol-ether compound represented by the formula (B) is a novel substance.

The polyol-ether compound thus obtained is a compound having at least three primary hydroxyl groups and an ether bond in combination in a molecule (the hydroxyl groups are arranged asymmetrically to the ether bond) and can be industrially used as raw materials for resins, paints and adhesives.

EXAMPLES

Now, the production method of the present invention will be more specifically described by way of Examples. The present invention is not limited to these Examples as long as it falls within the scope of the invention.

The results of a hydrogenation reduction reaction were evaluated based on the individual mole numbers of the raw material supplied, the raw material in a reaction solution and the polyol-ether compound produced, which were calculated based on the analysis by gas chromatography.

Conversion (%) of raw-material acetal(compound (1))=100×[1−(mole number of raw material remaining in reaction solution)/(mole number of raw material supplied)]

Selectivity of each polyol-ether compound produced (%)=100×(mole number of desired product)/ [(mole number of raw material supplied)−(mole number of raw material remaining in reaction solution)]

However, when isomers of a compound (1) are present, the sum of the values of isomers was used.

Analysis by gas chromatography was made by use of the following apparatus.

Apparatus: GC-2010 (product name), manufactured by Shimadzu Corporation

Column: DB-1 (product name), manufactured by Agilent Technologies

A compound (B) isolated was identified by $^1$H-NMR measurement and $^{13}$C-NMR measurement. The measurement conditions are shown below:

Apparatus: ECA500 (product name) manufactured by JEOL Ltd.

$^1$H-NMR

Nuclide: $^1$H

Measurement frequency: 500 MHz

Measurement sample: 5% $CD_3OD$ solution $^{13}$C-NMR

Nuclide: $^{13}$C

Measurement frequency: 125 MHz

Measurement sample: 5% $CD_3OD$ solution

The molecular weight of compound (B) was measured by GC-MS measurement (chemical ionization method [Cl+] and high resolution mass spectrometry [MS]). The measurement conditions are shown below.

Apparatus: Agilent 7890A (product name), manufactured by Agilent and

ACCU-TOF-GCV (JMS-T100GCV)(product name), manufactured by JEOL Ltd.,

GC measurement column: HP-5 (product name), manufactured by Agilent Technologies MS measurement conditions: chemical ionization method, ionization voltage 200 eV, ionization current 300 µA, detector voltage 1700 V A product was isolated by chromatography using the following materials Filler: "Wakogel C-200" (trade name) manufactured by Wako Pure Chemical Industries, Ltd.

Developing solvent: methanol-chloroform

A raw material for a reaction, i.e., compound (1) (cyclic acetal compound), was prepared by the following method.

Raw Material Preparation Example 1

(Preparation of 2-(5-ethyl-5-hydroxymethyl-[1,3]dioxan-2-yl)-2-methyl-propan-1-ol)

45.1 g of 2,2-dimethyl-3-hydroxy-propionaldehyde (hydroxypivalaldehyde, manufactured by Mitsubishi Gas Chemical Company Inc., purity 99.8%), 59.6 g of 2-ethyl-2-hydroxymethyl-propane-1,3-diol (trimethylolpropane, a reagent, manufactured by Tokyo Kasei Kogyo Co., Ltd.), 706 g of benzene and 5.0 g of granular Nafion ("NR-50" (trade name), a reagent manufactured by Sigma-Aldrich Corporation) were placed in a 2 L round bottom flask. While azeotropically distilling water generated under normal pressure together with benzene and removing out of the system by use of Dean-Stark trap, a reaction was performed until distillation of water was terminated. After the residue was filtered, the filtrate was concentrated, cooled to recrystallize. In this manner, a crystal of 2-(5-ethyl-5-hydroxymethyl-[1,3]dioxan-2-yl)-2-methyl-propan-1-ol (hereinafter, referred to as "compound HTPA") was obtained. The scheme of the synthesis reaction is shown below.

Synthesis reaction of compound (1) of
Raw-Material Preparation Example 1

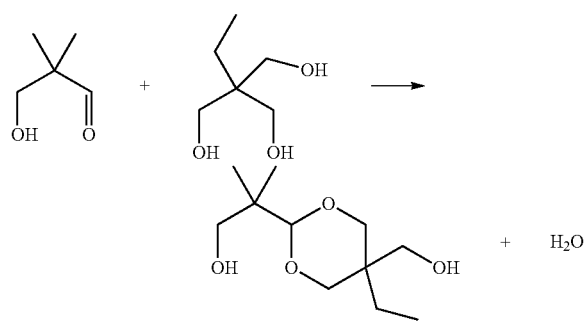

Raw Material Preparation Example 2

(Preparation of (2-(5-hydroxymethyl-5-methyl-[1,3]dioxan-2-yl)-2-methyl-propan-1-ol)

A crystal of 2-(5-hydroxymethyl-5-methyl-[1,3]dioxan-2-yl)-2-methyl-propan-1-ol (hereinafter, referred to as "compound HTEA") was obtained in the same manner as in Raw-Material Preparation Example 1 except that 89.3 g of 2,2-dimethyl-3-hydroxy-propionaldehyde (hydroxypivalaldehyde, manufactured by Mitsubishi Gas Chemical Company Inc., purity 99.8%) was used in place of 45.1 g of 2,2-dimethyl-3-hydroxy-propionaldehyde and 106.0 g of 2-hydroxymethyl-2-methyl-propane-1,3-diol (trimethylolethane, reagent, manufactured by Tokyo Kasei Kogyo Co., Ltd.) was used in place of 59.6 g of 2-ethyl-2-hydroxymethyl-propane-1,3-diol. The scheme of the synthesis reaction is shown below.

Synthesis reaction of compound (1) of
Raw-Material Preparation Example 2

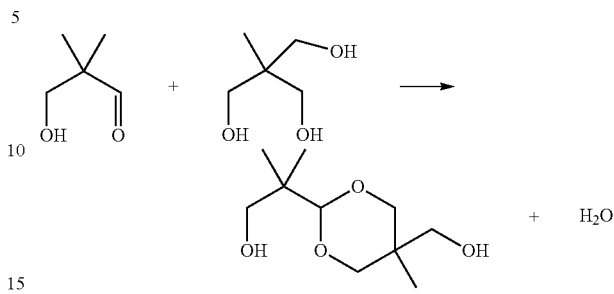

Raw Material Preparation Example 3

(Preparation of 2-(5,5-bis-hydroxymethyl-[1,3]dioxan-2-yl)-2-methyl-propan-1-ol)

A crystal of 2-(5,5-bis-hydroxymethyl-[1,3]dioxan-2-yl)-2-methyl-propan-1-ol (hereinafter, referred to as "compound HPEA") was obtained in the same manner as in Raw-Material Preparation Example 1 except that 27.3 g of 2,2-dimethyl-3-hydroxy-propionaldehyde (hydroxypivalaldehyde, manufactured by Mitsubishi Gas Chemical Company Inc., purity 99.8%) was used in place of 45.1 g of 2,2-dimethyl-3-hydroxy-propionaldehyde; 54.0 g of 2,2-bis-hydroxymethyl-propane-1,3-diol (pentaerythritol, reagent, manufactured by Tokyo Kasei Kogyo Co., Ltd.) was used in place of 59.6 g of 2-ethyl-2-hydroxymethyl-propane-1,3-diol, and a benzene-1,4-dioxane solution mixture was used in place of benzene. The scheme of the synthesis reaction is shown below.

Synthesis reaction of compound (1) of
Raw-Material Preparation Example 3

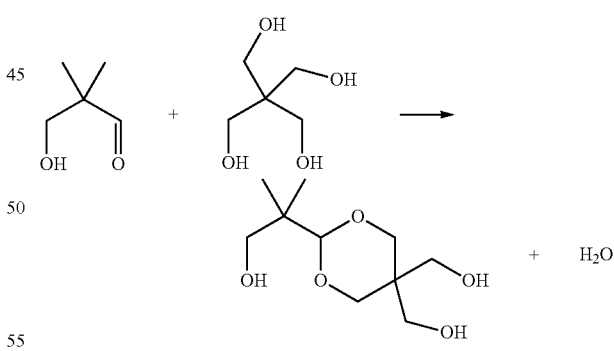

Carrier Preparation Example 1

Zirconium oxide used as a carrier for a metal component was prepared by the following method.

A white precipitation was obtained by dropping 15.5 g of 28% ammonia water to 505 g of a zirconium oxynitrate aqueous solution having a concentration of 25% by mass in terms of the zirconium oxide ($ZrO_2$) under stirring. This was filtered, and washed with ion-exchange water, followed by drying at 110° C. for 10 hours, to obtain hydrous zirconium oxide. This was placed in a porcelain crucible, and fired at 400° C. for 3 hours in air using an electric furnace. Then, the obtained fired product was ground in an agate mortar to obtain powdered zirconium oxide (hereinafter, represented as a "carrier A"). The BET specific surface area of the carrier A (measured by a nitrogen adsorption method, hereinafter the same applies) was 102.7 m²/g.

Carrier Preparation Example 2

An apatite compound used as a carrier for a metal component was prepared by the following method.

78.7 g of calcium nitrate tetrahydrate was dissolved in 300.5 g of ion-exchange water, and 260 mL of 28% ammonia water was added thereto. 26.4 g of diammonium hydrogen phosphate was dissolved in 500.6 g of ion-exchange water, and 150 mL of 28% ammonia water and 150 mL of ion-exchange water were added thereto. When the diammonium hydrogen phosphate-ammonia solution was added little by little to the calcium nitrate-ammonia solution under stirring, the obtained solution became cloudy gradually to obtain a white precipitation. After the end of addition, the solution was left after being stirred for about 2 hours. Then, the left precipitation was filtered and washed with ion-exchange water, followed by drying at 110° C. for 10 hours. Then, the dried product was fired at 500° C. for 3 hours in air using an electric furnace. Then, the fired product was ground in an agate mortar to obtain powdered apatite hydroxide (hereinafter, represented as a "carrier B"). The BET specific surface area of the carrier B was 60.7 m²/g.

Catalyst Preparation Example 1

A catalyst containing palladium as a specific metal component was prepared by the following method.

A 0.66% by mass palladium chloride-0.44% by mass sodium chloride aqueous solution was added to 5.0 g of a carrier A, to allow the metal component to be adsorbed on the carrier A. Then, a formaldehyde-sodium hydroxide aqueous solution was poured onto the carrier A to quickly reduce the adsorbed metal component. Then, the catalyst was washed with ion-exchange water and dried to prepare a 1.0% by mass palladium-supported zirconium oxide catalyst (hereinafter, represented as an "A1 catalyst").

Catalyst Preparation Example 2

A catalyst containing palladium as a specific metal component was prepared by the following method.

A 0.32% by mass palladium acetate-acetone solution was added to 5.0 g of a carrier B, to be adsorbed. Then, palladium acetate was supported on the carrier B by evaporating acetone to dryness. This was placed in a porcelain crucible, and fired at 400° C. for 3 hours in air using an electric furnace. The fired product was reduced at 110° C. under a hydrogen gas air current, to prepare a 1.0% by mass palladium-supported apatite catalyst (hereinafter, represented as a "B1 catalyst").

Catalyst Preparation Example 3

3.0 g of a B1 catalyst was added to a 5.9% by mass sodium chloride aqueous solution, and these were stirred for 2 hours, to perform ion exchange treatment. Then, the catalyst was filtration-washed with ion-exchange water, followed by drying, to prepare a 1.0% by mass palladium-supported catalyst (hereinafter, represented as a "B2 catalyst") of an apatite hydroxide carrier partially ion-exchanged to a chloride. As a result of elemental analysis by ICP emission analysis, the catalyst contained chlorine equivalent to about 5% of all hydroxyl groups.

The hydrogenation reduction reaction was performed by the following method.

Example 1

In a 100-mL reactor made of SUS (which is an abbreviated name of a stainless steel by Japanese Industrial Standards Committee), A1 catalyst (0.60 g), compound HTPA (2.0 g) and diisopropyl ether (24.0 g) were placed and the reactor was purged with nitrogen gas. Thereafter, the reactor was charged with hydrogen gas up to 8.5 MPa. The temperature was increased to a reaction temperature of 210° C. and the reaction was performed for 6 hours. Thereafter, the reactor was cooled and the content thereof was collected and analyzed by gas chromatography.

As a result, conversion of compound HTPA was 82.3% and selectivity to a product 2-ethyl-2-(3-hydroxy-2,2-dimethyl-propoxymethyl)-propane-1,3-diol (hereinafter, referred to as "compound NTPE") was 85.0%.

The reaction scheme in Example 1 is shown below.

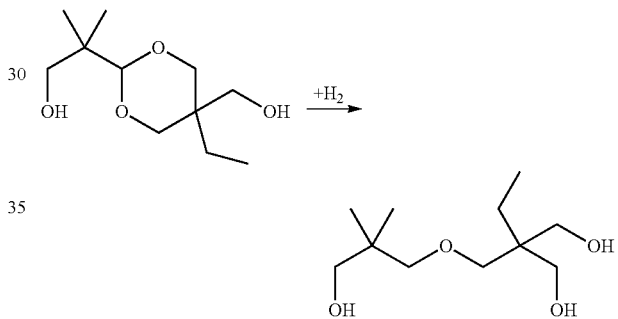

Example 2

The reaction was performed in the same manner as in Example 1 except that 1,4-dioxane (24.0 g) was used in place of diisopropyl ether (24.0 g); the reaction temperature was changed from 210° C. to 230° C.; and the reaction time was changed from 6 hours to 9 hours. As a result, the conversion of compound HTPA was 82.7% and the selectivity to compound NTPE was 79.8%.

Example 3

The reaction was performed in the same manner as in Example 2 except that B1 catalyst (1.00 g) was used in place of A1 catalyst (0.60 g). As a result, the conversion of compound HTPA was 82.6% and the selectivity to compound NTPE was 72.7%.

Example 4

The reaction was performed in the same manner as in Example 2 except that B2 catalyst (1.02 g) was used in place of A1 catalyst (0.60 g). As a result, the conversion of compound HTPA was 84.7% and the selectivity to compound NTPE was 76.8%.

Example 5

The reaction was performed in the same manner as in Example 2 except that n-hexane (24.0 g) was used in place of 1,4-dioxane (24.0 g). As a result, the conversion of compound HTPA was 86.9% and the selectivity to compound NTPE was 63.2%.

Example 6

The reaction was performed in the same manner as in Example 2 except that compound HTEA (1.8 g) was used in place of compound HTPA (2.0 g). As a result, the conversion of compound HTEA was 95.5% and the selectivity to a product 2-(3-hydroxy-2,2-dimethyl-propoxymethyl)-2-methyl-propane-1,3-diol was 79.4%.

The reaction scheme in Example 6 is shown below.

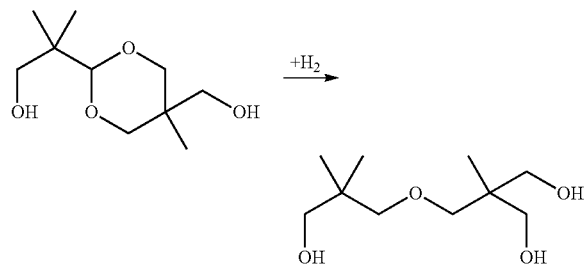

Example 7

The reaction was performed in the same manner as in Example 2 except that compound HPEA (1.8 g) was used in place of compound HTPA (2.0 g) and the reaction time was changed from 9 hours to 12 hours. As a result, the conversion of compound HPEA was 87.8% and the selectivity to a product, 3-(3-hydroxy-2,2-bis-hydroxymethyl-propoxy)-2,2-dimethyl-propan-1-ol (hereinafter, referred to as "compound NPEE") was 68.8%.

The reaction scheme in Example 7 is shown below.

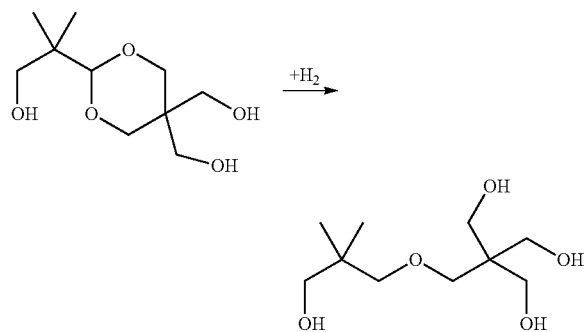

Compound NPEE was isolated by chromatography as mentioned above and the structure thereof was checked by NMR analysis.

(Compound NPEE)
$^1$H NMR (500 MHz, CD$_3$OD)
δ 0.84 (3H×2, s, Me$_2$C), 3.15, 3.30, 3.37 (2H×3, 3s, —CH$_2$—O—×2 & —CCMe$_2$CH$_2$OH), 3_57 (6H, s, —CH$_2$OH×3);
$^{13}$C NMR (125 MHz, CD$_3$OD)
δ 22.2, 37.7, 47.0, 63.3, 69.4, 71.8, 78.5.

The molecular weight of compound NPEE was measured by use of GC-MS analysis (chemical ionization method [CI+], high resolution mass spectrometry [MS]). In the mass spectrometry of chemical ionization method, as a molecule is analyzed without fragmentation, the information of molecular weight can be obtained. Furthermore, in the high resolution mass spectrometry, the molecular composition formula can be inspected by highly precise mass information. Protonated [M+H]$^+$ has a mass (molecular weight M+1) of 223.15570 while maintaining a molecular structure. From this, the composition formula of compound NPEE was determined as C$_{10}$H$_{22}$O$_5$.

The melting point of compound NPEE measured was 101° C., which was lower than the melting point (110° C.) of an analogue, a tetravalent alcohol, i.e., ditrimethylolpropane, and the melting point (260° C.) of pentaerythritol. From this, it was found that handling as e.g., a resin raw material is improved.

Catalyst Preparation Example 4

A catalyst containing platinum as a specific metal component was prepared by the following method.

To carrier A (5.0 g), an aqueous solution of 0.90% by mass potassium platinichloride was added to allow the metal component to adsorb onto the carrier A. To this, an aqueous solution of formaldehyde-sodium hydroxide was poured to reduce the adsorbed metal component. Then, the catalyst was washed with ion-exchange water and dried to prepare a zirconium oxide catalyst carrying 1.0% by mass platinum (hereinafter, referred to as "D1 catalyst").

Example 8

A reaction was performed in the same manner as in Example 2 except that D1 catalyst (2.42 g) was used in place of A1 catalyst (0.60 g). As a result, the conversion of compound HTPA was 48.0% and the selectivity to compound NTPE was 50.5%.

Example 9

A reaction was performed in the same manner as in Example 1 except that commercially available 5% by mass palladium-carrying alumina catalyst (product code: 163-13871, manufactured by Wako Pure Chemical Industries Ltd.) was used as a hydrogenation catalyst. As a result, the conversion of compound HTPA was 75.8% and the selectivity to compound NTPE was 61.5%.

Example 10

In a 600-mL reactor made of SUS, A1 catalyst (9.2 g), compound HTPA (61.3 g) and 1,4-dioxane (321 g) were placed. The reactor was purged with nitrogen gas. Thereafter, the reactor was charged with hydrogen gas up to 8.5 MPa. The temperature was increased to a reaction temperature of 230° C. and the reaction was performed for 6 hours. Thereafter, the reactor was cooled and the content thereof was collected and analyzed by gas chromatography. As a result, the conversion of compound HTPA was 97.7% and the selectivity to compound NTPE was 85.5%.

The present application is based on a Japanese Patent Application filed on Apr. 18, 2013 (Application No. 2013-087738), the content of which is incorporated herein by reference.

INDUSTRIAL APPLICABILITY

According to the production method of the present invention, a polyol-ether compound can be efficiently produced by hydrogenation reduction of a cyclic acetal compound (1) in the presence of a hydrogenation catalyst. In addition, a novel polyol-ether compound having an asymmetric structure can be obtained.

The invention claimed is:

1. A method for producing a polyol-ether compound, comprising:
subjecting a compound represented by the following formula (1) to hydrogenation reduction in the presence of a hydrogenation catalyst to obtain a polyol-ether compound represented by the following formula (2):

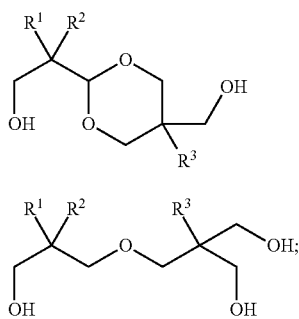

wherein:
$R^1$ and $R^2$, which may be the same as or different from each other, each represent a linear or branched alkyl group comprising 1 to 6 carbon atoms; and
$R^3$ represents a linear or branched alkyl group comprising 1 to 6 carbon atoms or a hydroxymethyl group.

2. The method according to claim 1, wherein $R^3$ is a methyl group or an ethyl group.

3. The method according to claim 1, wherein $R^3$ is a hydroxymethyl group.

4. The method according to claim 1, wherein $R^1$ and $R^2$ are each a methyl group.

5. The method according to claim 1, wherein the compound represented by the general formula (1) is subjected to hydrogenation reduction in a reaction solvent comprising an ether compound, a saturated hydrocarbon compound, or both.

6. The method according to claim 1, wherein the hydrogenation catalyst is a solid catalyst comprising palladium.

7. The method according to claim 1, wherein the hydrogenation catalyst is a solid catalyst comprising a zirconium compound or an apatite compound.

8. A polyol-ether compound represented by the following formula (3):

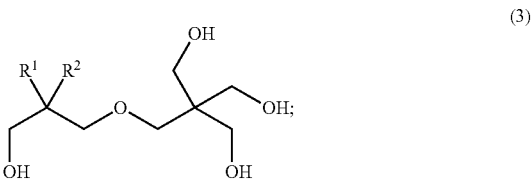

wherein $R^1$ and $R^2$, which may be the same as or different from each other, each represent a linear or branched alkyl group comprising 1 to 6 carbon atoms.

9. The polyol-ether compound according to claim 8, wherein $R^1$ and $R^2$ are each a methyl group.

10. The method according to claim 2, wherein $R^1$ and $R^2$ are each a methyl group.

11. The method according to claim 2, wherein the compound represented by the general formula (1) is subjected to hydrogenation reduction in a reaction solvent comprising an ether compound, a saturated hydrocarbon compound, or both.

12. The method according to claim 2, wherein the hydrogenation catalyst is a solid catalyst comprising palladium.

13. The method according to claim 2, wherein the hydrogenation catalyst is a solid catalyst comprising a zirconium compound or an apatite compound.

14. The method according to claim 3, wherein $R^1$ and $R^2$ are each a methyl group.

15. The method according to claim 3, wherein the compound represented by the general formula (1) is subjected to hydrogenation reduction in a reaction solvent comprising an ether compound, a saturated hydrocarbon compound, or both.

16. The method according to claim 3, wherein the hydrogenation catalyst is a solid catalyst comprising palladium.

17. The method according to claim 3, wherein the hydrogenation catalyst is a solid catalyst comprising a zirconium compound or an apatite compound.

18. The method according to claim 4, wherein the compound represented by the general formula (1) is subjected to hydrogenation reduction in a reaction solvent comprising an ether compound, a saturated hydrocarbon compound, or both.

19. The method according to claim 4, wherein the hydrogenation catalyst is a solid catalyst comprising palladium.

20. The method according to claim 4, wherein the hydrogenation catalyst is a solid catalyst comprising a zirconium compound or an apatite compound.

* * * * *